United States Patent [19]
Wildervanck et al.

[11] Patent Number: 6,051,734
[45] Date of Patent: Apr. 18, 2000

[54] PROCESS FOR THE OPTICAL RESOLUTION OF 3-(P-CHLOROPHENYL)-GLUTARAMIDE

[75] Inventors: Alexander Franciscus Wildervanck, Rosebank; Mino Rodolfo Caira, Newlands; Janet Lesley Scott, Woodstock; Liugi Renzo Nassimbeni, Rosebank; Rainer Clauss, Garfield; Barratt Robert Dixon Easter, Pinelands, all of South Africa

[73] Assignee: Farmarc Nederland B.V., Amsterda, Netherlands

[21] Appl. No.: 09/091,520

[22] PCT Filed: Dec. 16, 1996

[86] PCT No.: PCT/GB96/03103

§ 371 Date: Jun. 19, 1998

§ 102(e) Date: Jun. 19, 1998

[87] PCT Pub. No.: WO97/22578

PCT Pub. Date: Jun. 26, 1997

[30] Foreign Application Priority Data

Dec. 20, 1995 [ZA] South Africa ............ 95/10844

[51] Int. Cl.$^7$ ............ C07C 229/00; C07C 233/00
[52] U.S. Cl. ............ 562/573; 562/540; 564/123
[58] Field of Search ............ 562/573, 540; 564/123

[56] References Cited

FOREIGN PATENT DOCUMENTS

| 234 162 A3 | 3/1986 | Germany ............ C07C 101/10 |
| 42 24 342 A1 | 1/1994 | Germany ............ C07D 207/28 |
| 6407755 | 1/1965 | Netherlands . |

OTHER PUBLICATIONS

Herdeis et al, Tetrahedron:Asymmetry, 3(9):1213–1221 (1992).
Schoenfelder et al, Synlett, 2:63–64 (1993).
Chenevert et al, Can. J. Chem., 72:2312–2317 (1994).
Allan et al, Aust. J. Chem, 34:2641–5 (1981).
Sioufi et al, J. Chromatogr., 450:222 (1988).
Wuis et al, J. Chromatography, 415:419–422 (1987).
Allenmark et al, Chirality, 1:154–160 (1989).
Vaccher et al, J. Chromatography, 645:95–99 (1993).
Sano et al, Kuromatogurafi, 15(4):234–5 (1994).
Weatherby et al, J. Neurosci. Methods, 10:23–28 (1984).
Vaccher et al, J. Chromatography, 542:502–507 (1991).

*Primary Examiner*—Gary L. Kunz
*Assistant Examiner*—Everett White
*Attorney, Agent, or Firm*—Pillsbury Madison & Sutro LLP

[57] ABSTRACT

A process for the optical resolution of racemic 3-(p-chlorophenyl)glutaramide (GAM) into its R isomer R—COOH and its S isomer S—COOH, which process includes the steps of either:

(1) reacting racemic 3-(p-chlorophenyl)-glutaramide dissolved in a suitable solvent with S-(−)-α-methylbenzylamine of the formula $H_2N$—S'

(2) precipitating out of the solution of step (1) R—$CO_2^-$.$H_3^+N$—S';

(3) dissolving the precipitate of step (2) in water, with the addition of a suitable acid; and (4) precipitating out of the solution of step (3) R—COOH; or (5) reacting racemic -3-(p-chlorophenyl)-glutaramide dissolved in a suitable solvent with R-(+)-α-methylbenzylamine of the formula $H_2N$—R';

(6) precipitating out of the solution of step (5) S—$CO_2^-$.$H_3^+N$—R';

(7) dissolving the precipitate of step (6) in water, with the addition of a suitable acid, and (8) precipitating out of the solution of step (7) S—COOH.

The R isomer of GAM may be used for the production of R-baclofen and the S isomer of GAM may be used for the production of S-baclofen.

17 Claims, 7 Drawing Sheets

PROCESS FOR THE OPTICAL RESOLUTION OF 3-(P-CHLOROPHENYL)-GLUTARAMIDE

This application is the national phase of international application PCT/GB96/03103 filed Dec. 16, 1996 which designated the U.S.

BACKGROUND OF THE INVENTION

This invention relates to a process for the optical resolution of racemic 3-(p-chlorophenyl)-glutaramide (GAN) into its R and S isomers, and to the use of the R isomer for the production of R-baclofen or the use of the S isomer for the production of S-baclofen.

The biological activity and physical properties of racemic baclofen are well documented in the literature[1,2]. Further extensive pharmacological tests have concluded that the biological activity of the drug resides with the R-enantiomer (R-baclofen)[3]. These selective activities have led to extensive research concerning methods of separating the optical isomers of baclofen. Several methods of resolution have since appeared in the literature. These are mainly chromatographic separations[4-9], making use of either bonded chiral stationary phases, or mobile phases with chiral modifiers. Other methods include asymmetric syntheses[10-12] as well as a chemoenzymatic synthesis[13].

As is apparent from the literature, most chromatographic separations involve precolumn derivatization implying some form of protection and subsequent deprotection. Where the formation of covalent diastereomers is not necessary, the columns used involved either relatively expensive chiral stationary phases or chiral modifiers in the mobile phase. The asymmetric syntheses are mostly time consuming multistep reactions with relatively low yields.

The compound α-methylbenzylamine (MBA) is well known as a resolving agent in both covalent and dissociable diastereomer techniques[16]. MBA is a strong base widely used for resolution of acidic racemates and in particular carboxylic acids. Examples are MBA mandelate[17], MBA phenylbutyrate[18] and MBA hydrotropate[19] salts. Concerning drug resolution, a good example is the early separation of the antibacterial fosfomycin[20].

SUMMARY OF THE INVENTION

According to a first aspect of the invention there is provided a process for the optical resolution of racemic 3-(p-chlorophenyl)glutaramide into its R isomer:

R—COOH
    wherein R is

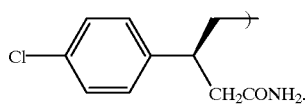

and its S isomer:

S—COOH
    wherein S is

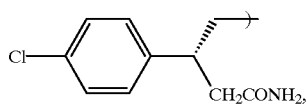

which process includes the steps of either:

(1) reacting racemic 3-(p-chlorophenyl)-glutaramide dissolved in a suitable solvent with S-(-)-α-methylbenzylamine of the formula: $H_2N$—S'
    wherein S' is

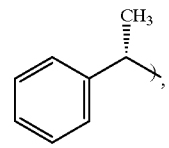

(2) precipitating out of the solution of step (1) R—$CO_2^-$ $H_3^+N$—S';

(3) dissolving the precipitate of step (2) in water, with the addition of a suitable acid; and (4) precipitating out of the solution of step (3) R—COOH; or (5) reacting racemic-3-(p-chlorophenyl)-glutaramide dissolved in a suitable solvent with R-(+)-α-methylbenzylamine of the formula $H_2N$—R'
    wherein R' is

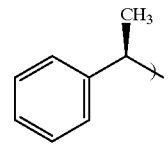

(6) precipitating out of the solution of step (5) S—$CO_2^-$ $H_3+N$—R';

(7) dissolving the precipitate of step (6) in water, with the addition of a suitable acid, and (8) precipitating out of the solution of step (7) S—COOH.

The precipitation of either salt is controlled by the choice of base resolving agent, i.e either S- or R-α-methylbenzylamine. In each case two salts are formed but these have vastly differing solubilities and thus only one of these is precipitated.

When S-(—)-α-methylbenzylamine $H_2N$—S' is reacted with racemic GAM (R,S—COOH) the following salts are formed: R—$CO_2^-H_3^+N$—S' and S—$CO_2^-.H_3^{+N—S'}$.

However R—$CO_2^-H_3^+N$—S' is much less soluble than S—$CO_2^-H_3^+N$—S' and therefore precipitates from solution and can be filtered off. The opposite occurs when R-(+)-α-methylbenzylamine (R') is reacted with racemic GAM although the conditions may be identical in each case.

In step (1) and step (5), a suitable solvent is for example a lower alkanol such as methanol.

Step (1) and step (5) are preferably carried out at an elevated temperature up to about 60° C.

In step (2) and step (6), the solution of step (1) or step (5), respectively, is allowed to stand, preferably in the absence of light, for a period of time, to allow precipitation to occur. Thereafter, the precipitated crystals may be filtered off, and dried.

In step (3) and step (7) the crystals of step (2) or step (6), respectively, are dissolved in water, preferably at an elevated temperature up to about 90° C. Thereafter, there is added a suitable acid, such as for example hydrochloric acid or sulfuric acid.

In step (4) and step (8) the solution of step (3) or step (7), respectively, is allowed to cool to room temperature or below so that precipitation may occur. Thereafter, the precipitate may be filtered off, washed and dried to give the desired R-isomer of GEM, or the S-isomer of GAM, respectively.

According to a second aspect of the invention there is provided the compound

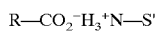

wherein R and S' are as defined above.

According to a third aspect of the invention there is provided the compound

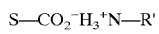

wherein S and R' are as defined above.

According to a fourth aspect of the invention there is provided the use of the R-isomer of GAM, produced by the process described above, in the production of R-baclofen.

According to a fifth aspect of the invention there is provided the use of the S-isomer of GAM, produced by the process described above, in the production of S-baclofen.

BRIEF DESCRIPTION OF THE DRAWINGS

The definition of P and N salts is taken from Ugi[21], where P refers to the salt in which substrate and resolving agent are of like sign and N to the salt in which substrate and resolving agent are of unlike sign.

DESCRIPTION OF EMBODIMENTS

Figure 1A:
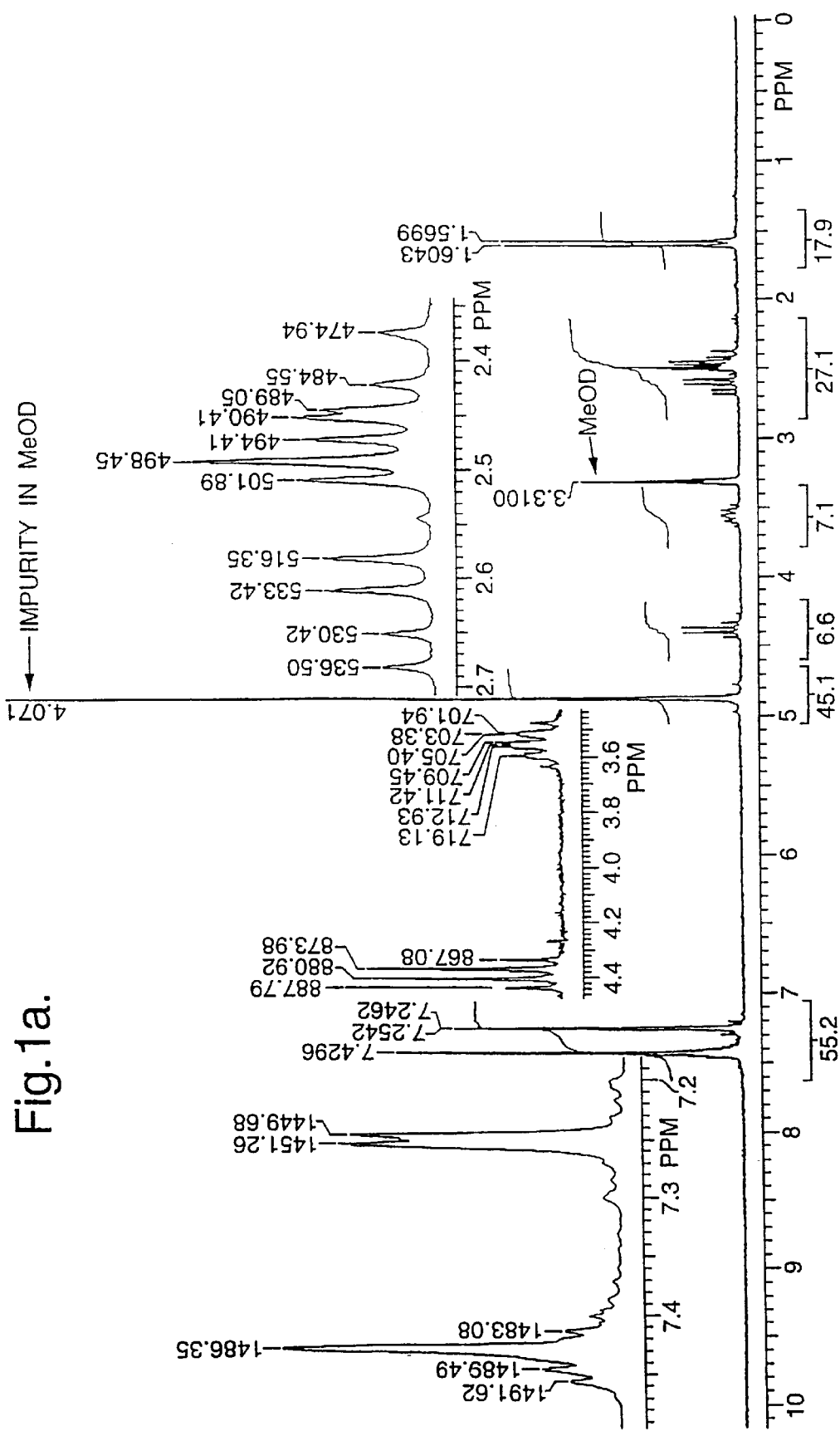
FIGS. 1(a) to 1(c) are NMR spectra of (a)N-salt, (b) (R,S)GAM and (c) R-GAM.

The crux of the invention is a process for the optical resolution of racemic-GAM into its R isomer and its S isomer, and then the use of the R isomer in the production of R-baclofen, and the S isomer in the production of S-baclofen.

The process makes use of the principle of dissociable diastereomers, making use of the differential physical properties of organic acid-base diastereomeric salts.

Two examples of the resolution of racemic GAM to give R-GAM will now be given.

EXAMPLE 1

GAM (18 g, 74.4 mmol) was dissolved in methanol (250 ml) and warmed to about 60° C. S-MBA (9.48 ml, 74.4 mmol) was carefully added via a graduated pipette, and the warm solution stirred for a few minutes. The resulting 1:1 GAMMBA solution was cooled to room temperature and left standing in a dark place for about 24 hours affording colorless plate-like crystals (9.86 g, 73% yield (as calculated for one enantiomer)). The crystals were filtered off, dried and dissolved in water (200 ml) by heating to about 90° C. 3M HCl (90.5 ml) was added at this temperature after which the solution was allowed to cool to room temperature (or even refrigerated). The precipitate was filtered off at the pump, washed with water and vacuum dried to give R-GAM (6.23 g, 95% yield, 69% overall yield).

EXAMPLE 2

GAM (1400 g, 5.79 mol) was dissolved in refluxing methanol (11,0 l). S-MBA (756 ml, 5.93 mol) was slowly added with stirring and the resulting GAMMBA solution cooled slowly to ambient temperature affording colorless crystals. The crystalline GAMMBA salt was filtered off, washed with a little methanol, and dried (651 g, 62% yield (as calculated for one enantiomer)). The GAMMBA salt (650 g, 1.79 mol) was dissolved in refluxing methanol (9.0 l) and the solution allowed to cool to ambient temperature. Crystals were filtered off, washed with a little methanol, and dried (356 g, 55% yield). Recrystallised R-GAMMBA salt (356 g, 0.98 mol) was dissolved in hot water (9.5 l at 95° C.) and 5 M HCl added (310ml). The suspension was cooled to 0–5° C. and the resultant R-GAM precipitate filtered off, washed with chilled water and dried (223 g, 94% yield, 32% overall yield).

Example 2 gives a product with a slightly higher degree of optical purity.

An example of the resolution of racemic GAM to give S-GAM will now be given.

EXAMPLE 3

(R,S)-GAM (27.72 g, 114.7 mmol) was dissolved in refluxing methanol (300 ml) and R-MBA (15 ml, 117.5 mmol) added. Methanol was added to make the solution up to ca 400 ml to dissolve all material. After cooling for 2.5 hours, acetone (10 ml) was added. The solution was allowed to crystallize for 24 hours and the crystals so formed filtered off, washed with methanol/acetone and dried (8.5 g, 40% yield). This experiment was repeated a number of times on a similar scale to produce a larger quantity of S-GAMR-MBA salt.

GAMMBA salt (14.5 g, 40.0 mmol) was dissolved in refluxing methanol (220 ml) and the solution allowed to cool. The crystals so obtained were filtered off, washed with methanol, and dried (8.74 g, 60% yield). S-GAMMBA salt (8.74 g, 24.1 mmol) was dissolved in hot water (300 ml at ca 80–90° C.) and 0.3M HCl (82 ml, 24.6 mmol) added. The resultant suspension was chilled to 5° C. and the precipitate filtered off, washed with water and dried (4.54 g, 78% yield, 18.7% overall yield).

The conversion of GAM to baclofen is known as the Hofmann rearrangement and proceeds under relatively mild conditions with retention of configuration[14,5].

Examples of the conversion of the R isomer of GAM to R-baclofen and the S isomer of GAM to S-baclofen will now be given.

EXAMPLE 4

To a solution of sodium hydroxide (2.8 g, 69.4 mmol) in water (50 ml) was added R-GAM from Example 1 (6.57 g, 27.21 mmol) at about 20° C. A 10.8% aqueous solution of sodium hypochlorite (28.3 g) was then added over 2.5 hours at 0° C. via a dropping funnel. The solution was stirred for a further 12 hours at room temperature (about 20° C.) after which time it was carefully neutralized (pH 7.5) with dilute hydrochloric acid. The precipitate was filtered off at the pump, washed with water and acetone. The precipitate was then boiled in methanol to remove the last traces of GAM and filtered to yield pure R-baclofen (1.3 g, 22% yield). The mother liquors were reduced in volume in vacuo to yield more product which was boiled in methanol and filtered to give another 2.05 g of R-baclofen (3.35 g total, 57.6% yield).

A portion of R-baclofen was then converted to its hydrochloride by treatment with concentrated HCl.

EXAMPLE 5

To a solution of sodium hydroxide at 25° C. (47.0 g, 1.18 mol) was added R-GAM from Example 2, (111.4 g, 0.46 mol). A 9.8% aqueous solution of sodium hypochlorite (530 g, 0.696 mol) was added dropwise over 2 hours while the solution was maintained at 0–5° C. The solution was allowed to warm to 25° C. after 1 hour and stirred for 24 hours at 25° C. The pH was adjusted, by addition of concentrated hydrochloric acid, to 7.5. Crude R-baclofen was filtered off and washed with water. Further purification yielded R-baclofen (23 g, 35% yield) which contained no detectable traces of S-baclofen (>99.6% ee).

EXAMPLE 6

Sodium hydroxide (1.92 g, 47.9 mmol) was dissolved in water (35 ml) and cooled to 20° C. S-GAM from Example 3, (4.5 g, 18.79 mmol) was added with stirring. The solution was cooled in an ice bath and sodium hypochlorite solution (19.39 g) added over a period of 2.5 hours. The solution was allowed to warm to ambient temperature and was stirred for a further 5 hours. pH was adjusted to 7 to 8 by dropwise addition of concentrate hydrochloric acid and the resultant precipitate filtered off, washed with water followed by hot acetone/methanol and dried (0.95 g, 23% yield).

Figure 1B:
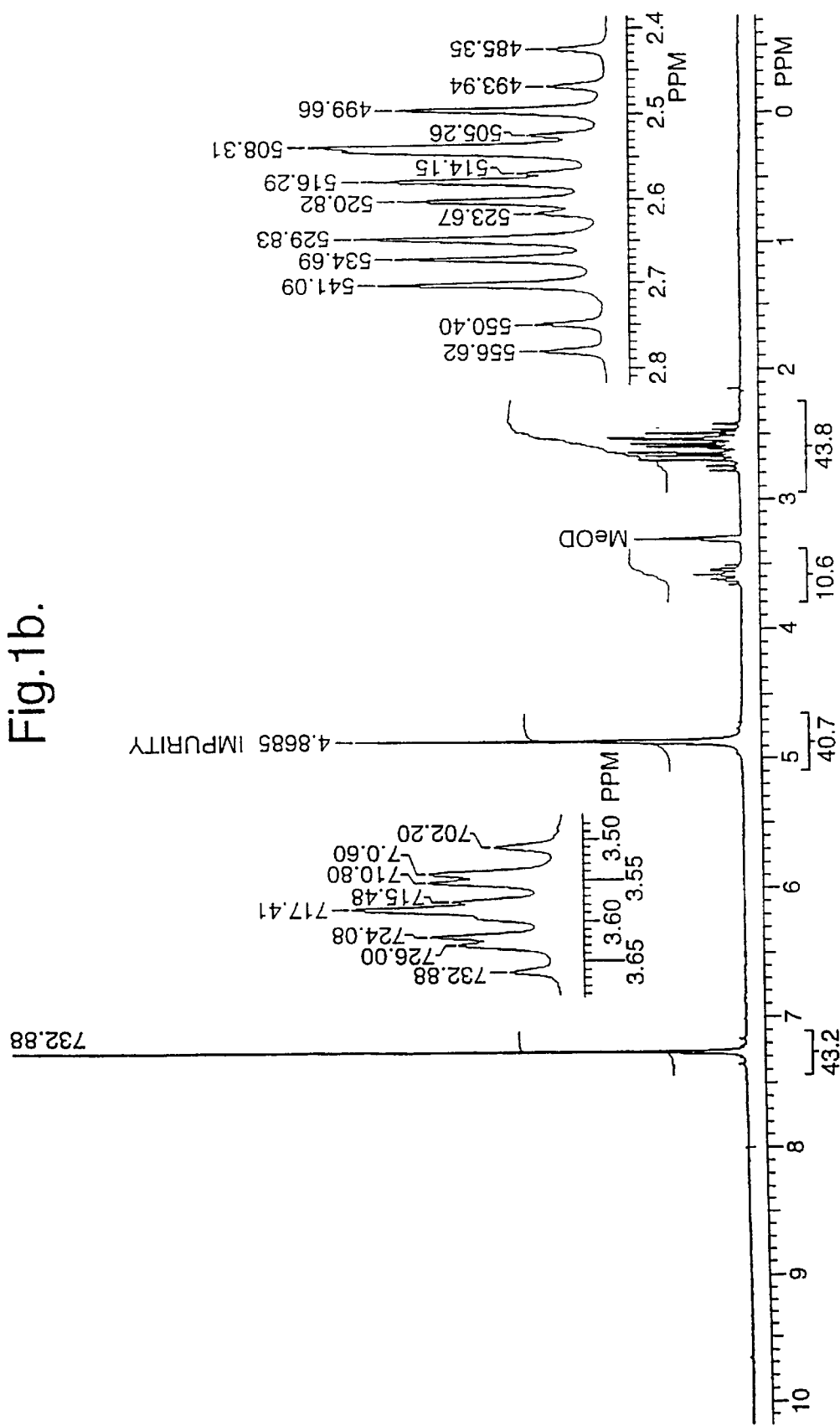
Figure 1C:
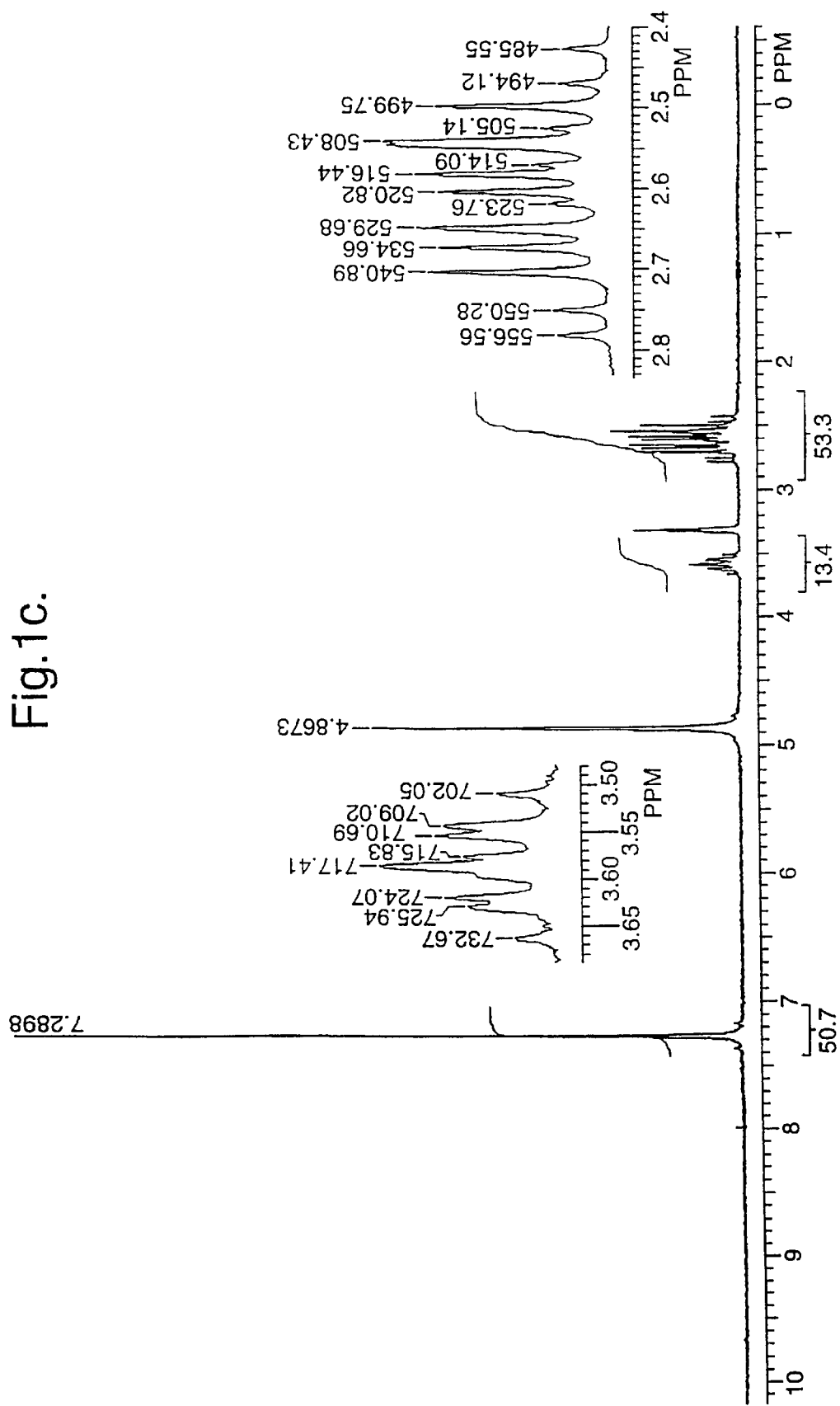
Figure 2:
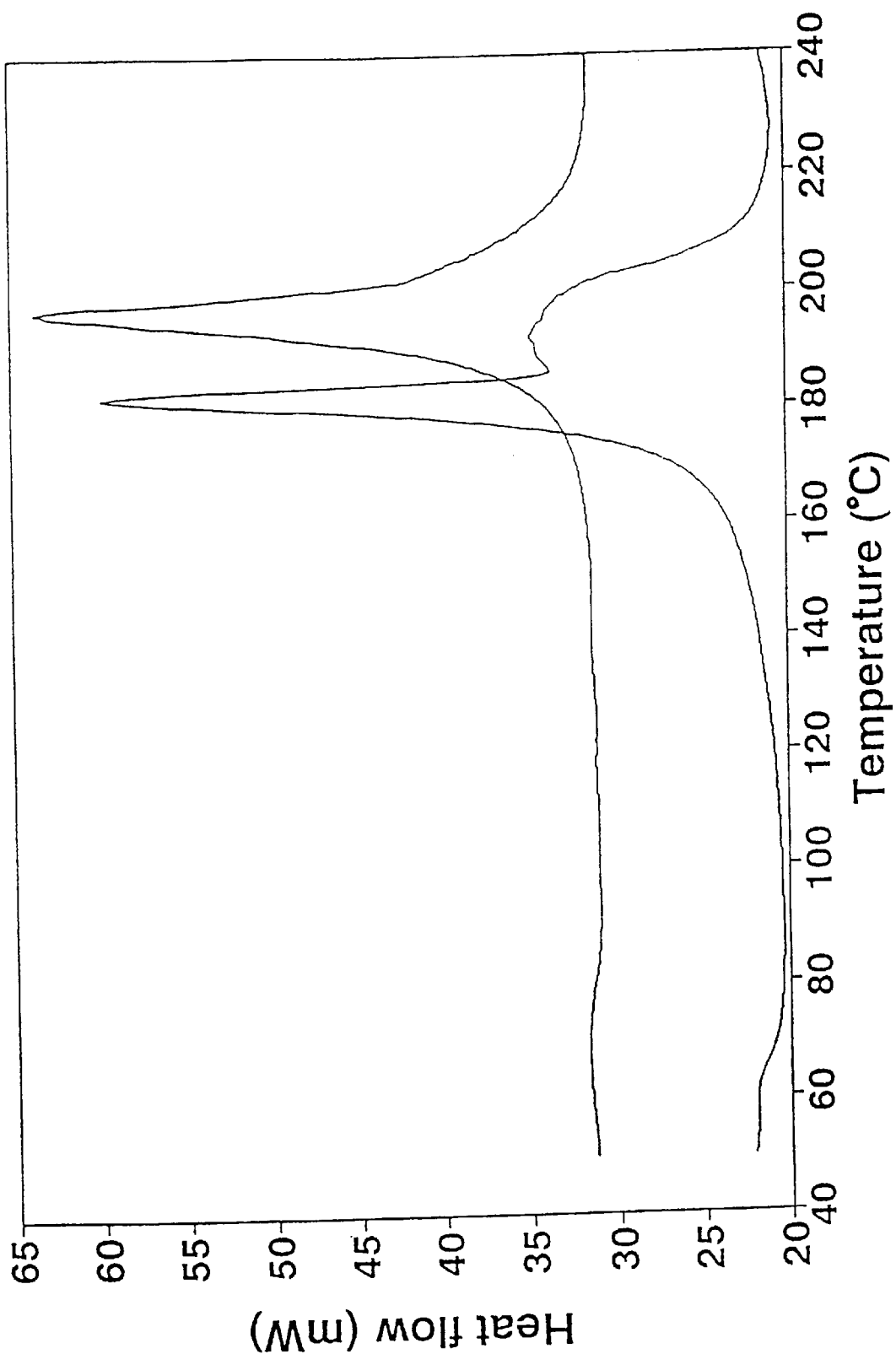
FIG. 2 is a differential scanning calorimetry trace of the N salt (solid) and of the P salt contaminated with N salt (dotted)

Various analyses of the compounds utilized in the present invention have been carried out, and these are set out below.
NMR The GAM:MBA ratio was initially established by NMR spectroscopy. The samples were run in CD$_3$OD (see FIG. 1). The integration of the two protons bonded to the chiral carbons viz. $\delta_H$ 4.4(1H,q, Ph-CH(CH$_3$)NH$_2$) and 3.5(1H, m,—CH(CH$_2$CONH$_2$)(CH$_2$CO$_2$H) provided first evidence of a 1:1 ratio. (see FIG. 1). The final product R-GAM was also characterized by NMR. The spectrum was identical to that of racemic GAM (starting material), proving the product to be the free acid (see FIGS. 1b and 1c).
Thermal Analysis Differential Scanning Calorimetry (DSC) showed the same melting point for both diastereomeric salts (187° C.) by a characteristic broad endotherm (see FIG. 2). The diagram also shows a DSC trace of the P salt contaminated with the N salt. Either salt, when contaminated with the opposite diastereomer, exhibited a lowering of the melting point. Both racemic and enantiomerically pure GAM melt at 173° C., and the R-baclofen at 205–208° C.
Microanalysis

|  | C | H | N |
|---|---|---|---|
| Calculated for salt | 62.89% | 6.34% | 7.72% |
| Found: | 62.37% | 6.40% | 7.65% |
| Calculated for R-(+)-GAM | 54.67% | 4.96% | 5.79% |
| Found: | 54.62% | 4.98% | 5.72% |
| Calculated for R-(−)-Baclofen | 56.21% | 5.66% | 6.56% |
| Found: | 56.30% | 5.78% | 6.52% |

X-ray Powder Diffractometry

Figure 4A:
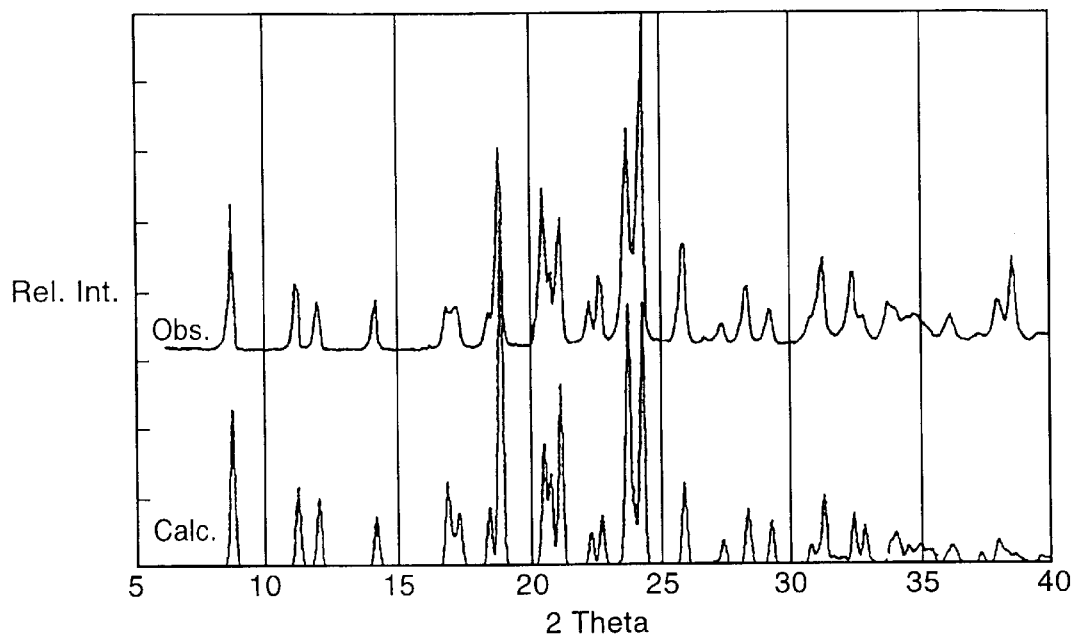
FIGS. 4(a) to 4(d) are the X-ray powder diffractometry spectra of (a) the N salt (calculated and observed), (b) the P salt (calculated and observed), (c) the enantiomers of GAM, and (d) R-(-)-baclofen monohydrochloride.
Figure 4B:
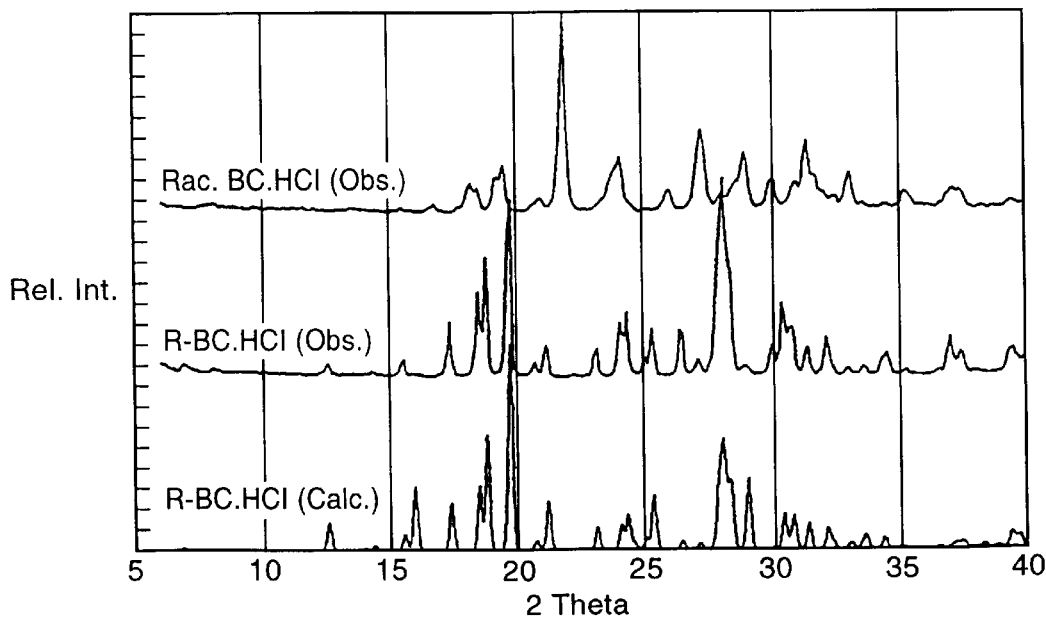

FIGS. 4a and 4b show the XRD powder patterns of the N and P salts. These traces are distinctly different proving the existence of two different crystal structures. The powder patterns were also calculated from the single crystal structure data and these agreed well with the measured patterns of the ground crystals obtained from the bulk samples.

Figure 4C:
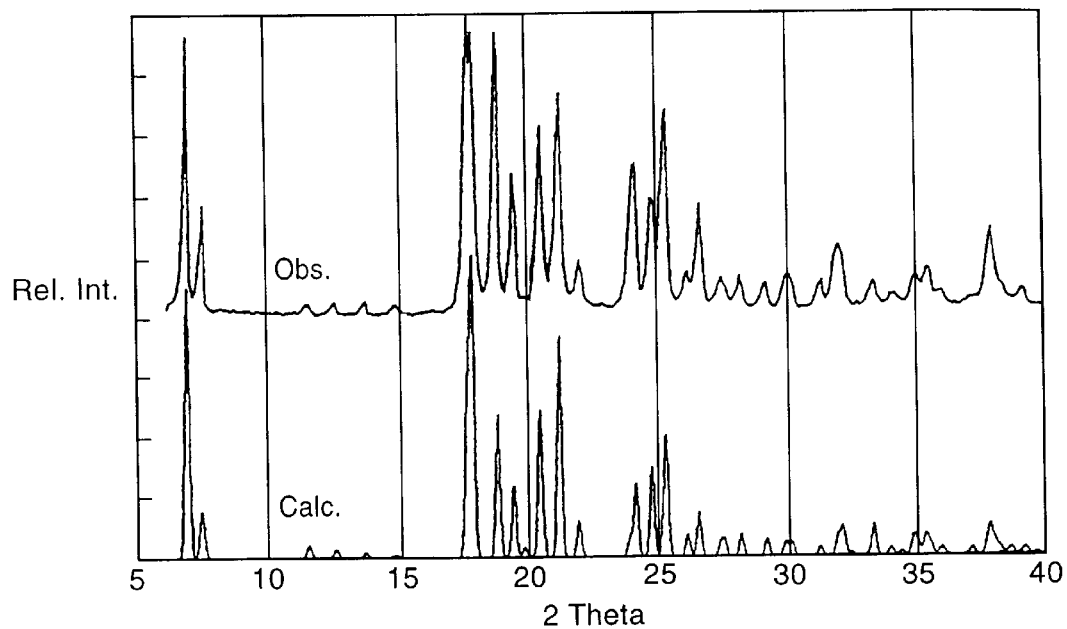

FIG. 4c indicates that (R.S) GAM crystallizes as racemic crystals, since its crystal structure differs from those of its R and S enantiomers. The S enantiomer was isolated from the P salt that remained in the mother liquor after removal of the N salt precipitate. The P salt was purified by using a different solvent system (ethanol and ethyl acetate).

Figure 4D:
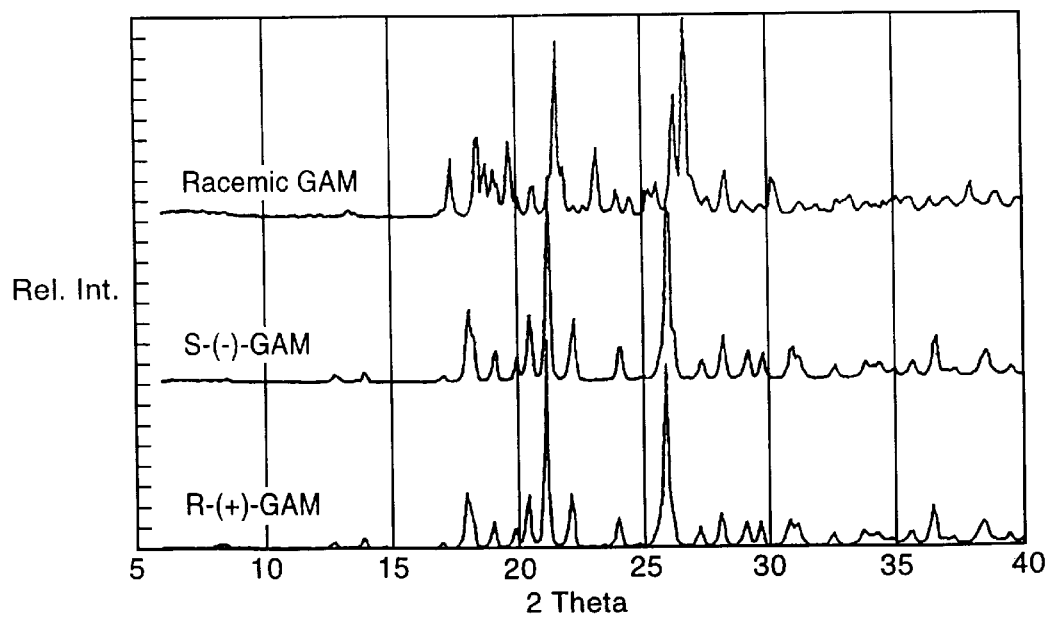

The crystal structure of R-baclofen hydrochloride (R-BACHCl) has been published[22]. FIG. 4d shows the good agreement between the powder pattern computed from the published data and the powder pattern measured from the sample of R-BACHCl from the above example. The intense peaks in the powder pattern of racemic BACHCl do not have counterparts in the R-BACHCl powder pattern.
Polarimetry

|  | N salt R-GAMS-MBA | P salt S-GAMS-MBA | R-GAM |
|---|---|---|---|
| 589 | +5.5° | −13.7° | +9.5° |
| 546 | +6.8° | −16.7° | +11.0° |
| 436 | +11.1° | −28.8° | +18.8° |
| 365 | +16.0° | −48.2° | +30.4° |

Figure 3:
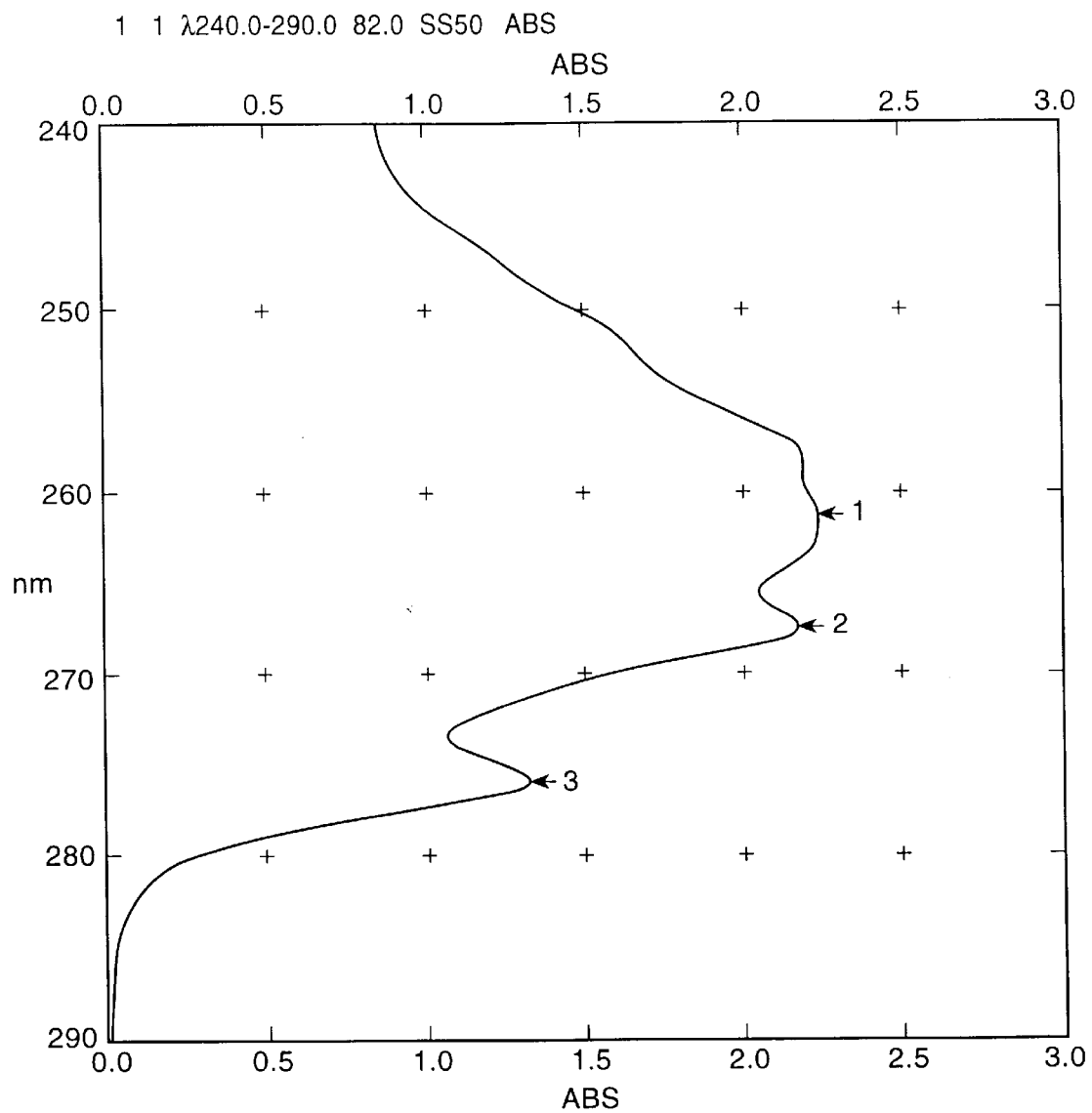
FIG. 3 is the UV absorption spectrum of GAMMBS salt (ca 2 mg/ml solution)

These values remained constant after further recrystallizations.
Solubility Determination Since the difference in solubility of the two diastereomeric salts forms the basis of their separation, the concentrations at 24° C. of the saturated solutions of P and N salts were determined by UV spectroscopy. FIG. 3 shows the UV absorption spectrum of the salts between λ=230 and 290 nm. Standard solutions were made in the concentrating range 0.25–1.5 mg/ml solution. The absorbances of the solutions were measured at $\lambda_{max}$=260.6 nm. From the absorbance of the solutions saturated at 24° C. and diluted 1:100, the solubilities were calculated to be (in methanol):

P salt 123 mg/ml solution

N salt 30.6 mg/ml solution

The fact that the solubilities differ by a factor of about 4 confirms the ease and speed with which this separation can be performed.

The racemic GAM to R-baclofen conversion gives a 32% overall yield. Furthermore, the enantiomeric purity of the resolved material is estimated at greater than 99.8%.

References

1 Brogden R N et al, Drugs 8(1974) p 1.

2 S. Ahuja in Analytical Profiles of Drug Substances, vol 14. K. Florey, Ed. (Academic Press, New York, (1985) 527–548.

3 H.R. Olpe, H Demieville, V. Baltzer, W L Bencze, W P Koella, P Wolf and H L Hess, Eur. J Pharmacol., 52 (1978) 133–136.

4 E W Wuis, E W J Benekom Kolmer, L E C van Beijsterveld, R C M Burgers, T B Vree and E van der Kleyn. J Chromatogr. 451 (1987) 419.

5 S Allenmark, S Andersson. Chirality. 1:154 (1989) 160.

6 C Vaccher, P Berthelot, M Debaert, J Chromatogr., 645(1) (1993) 95.

7 A Sano, S Takitani, H Nakamura, Kuromaogurafi 15(4), (1994) 234–5.

8 R P Weatherby, R D Allen and G A R Johnston, J Neurosci. Methods. 10 (1984) 23.

9 C Vaccher, P Berthelot, N Flouquet, M Debaert, J Chromatogr, 542 (1991) 502–507.
10 C Herdies and H P Hubmann, Tetrahedron: Asymmetry. 3(9) (1992) 1213–1221.
11 H P Hubmann, C Herdies DE 4,224,342, Jan 27, 1994.
12 A Shoenfelder, A Mann, S Le Coz.Synlett. 1 (1993) 63–64.
13 R Chenevert and M Desjardins, Can. J. Chem. 72 (1994) 2312–2317.
14 Neth. Appl 6407755, Jan 11, 1965.
15 DD 234162, Mar. 26, 1986.
16 J Jacques, A Collet S H Wilen. Enantiomers, Racemates and Resolutions. Krieger, Fla., 1991.
17 S Larsen, H Lopez de Diego, J Chem. Soc. Perkin Trans. 2 (1993) 469–473.
18 M C Brianso, Acta Crystallogr. B34, 1978,679.
19 M C Brianso, Acta Crystallogr. B32, 1976,3040.
20 E J Glamkowsky, G Gal, R Purick, A J Davidson and M Sletzinger, J. Org. Chem. 35(10) (1970) 3510–3512.
21 I Ugi, Z. Naturforsch. 20B (1965)405.
22 C H Chang, D S C Yang, C Y Chung, W BiCheng, J Pletcher, M Sax, and C F Terrence, Acta cryst. B38 (1982)2065–2067.

We claim:

1. A process for the optical resolution of racemic 3-(p-chlorophenyl)glutaramide into its R isomer:

R-COOH
wherein R is

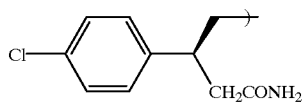

and its S isomer;

S-COOH wherein S is

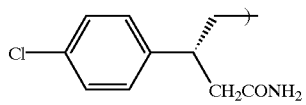

which process includes the steps of either;

(1) reacting racemic 3-(p-chlorophenyl)-glutaramide dissolved in a suitable solvent with S-(—)-α-methylbenzylamine of the formula: $H_2N$-S'
wherein S' is

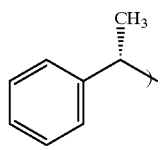

(2) precipitating out of the solution of step (1) R-$CO_2^-$ $H_3^+$N-S';
(3) dissolving the precipitate of step (2) in water, with the addition of a suitable acid; and
(4) precipitating out of the solution of step (3) R-COOH; or (5) reacting racemic —3-(p-chlorophenyl)-glutaramide dissolved in a suitable solvent with R-(+)-β-methylbenzylamine of the formula: $H_2N$-R' wherein R' is

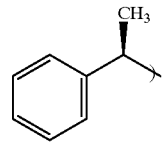

(6) precipitating out of the solution of step (5) S-$CO_2^-$ $H_3^+$N-R';
(7) dissolving the precipitate of step (6) in water, with the addition of a suitable acid; and
(8) precipitating out of the solution of step (7) S-COOH.

2. A process according to claim 1 wherein in step (1) the solvent is a lower alcohol.

3. A process according to claim 2 wherein in step (1) the solvent is methanol.

4. A process according to any one of claims 1 to 3 wherein step (1) is carried out at an elevated temperature up to about 60° C.

5. A process according to claim 1 wherin in step (2) the solution of step (1) is allowed to stand for a period of time to allow precipitation to occur.

6. A process according to claim 1 wherein in step (3) the crystals of step (2) are dissolved in water and then there is added an acid selected from the group consisting of hydrochloric acid and sulfuric acid.

7. A process according to claim 1 wherein in step (4) the solution of step (3) is allowed to cool to room temperature or below so that precipitation occurs.

8. A process according to claim 1 wherein in step (5) the solvent is a lower alcohol.

9. A process according to claim 8 wherein in step (5) the solvent is methanol.

10. A process according to claim 1 wherein step (5) is carried out at an elevated temperature up to about 60° C.

11. A process according to claim 1 wherein in step (6) the solution of step (5) is allowed to stand for a period of time to allow precipitation to occur.

12. A process according to claim 1 wherein in step (7) the precipitate of step (6) is dissolved in water and that there is added an acid selected from the group consisting of hydrochloric acid and sulfuric acid.

13. A process according to claim 1 wherein in step (8) the solution of step (7) is allowed to cool to room temperature or below so that precipitation occurs.

14. The process which comprises converting the R-isomer of 3-(p-chlorophenyl)-glutaramide, obtained from the process of claim 1, to R-baclofen by Hoffmann rearrangement.

15. The process which comprises converting the S-isomer of 3-(p-chlorophenyl)-glutaramide, obtained from the process of claim 1, to S-baclofen by Hoffmann rearrangement.

16. A compound having a formula:
R-CO$_2^-$H$_3^+$N-S'
wherein R is
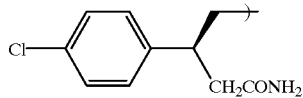
and S' is
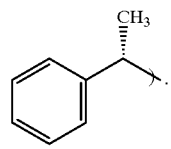
17. A compound having a formula:
S-CO$_2^-$H$_3^+$N-R'
wherein S is
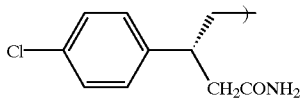
and S' is
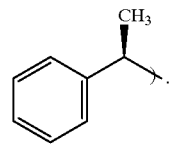
* * * * *

UNITED STATES PATENT AND TRADEMARK OFFICE
CERTIFICATE OF CORRECTION

PATENT NO.   : 6,051,734
DATED        : April 18, 2000
INVENTOR(S)  : Wildervanck et al.

It is certified that error appears in the above-identified patent and that said Letters Patent is hereby corrected as shown below:

Drawings,
Please relabel the drawings as follows:
Fig. 4b should read -- Fig. 4d --;
Fig. 4c should read -- Fig. 4b --; and
Fig. 4d should read -- Fig. 4c --.

Column 1,
Line 10, change "(GAN)" to -- (GAM) --.

Column 2,
Line 2, change "3-(p-chioropheyl)" to -- 3-(p-chlorophenyl) --;
Line 34, after "S—$CO_2^-$ " insert -- • --;
Line 35, change "$H_3$+N—R'" to -- $H_{3+}$N—R' --;
Line 46, change "R—$CO_2^-$ $H_3$-$^+$N—S'" to -- R—$CO_2^-$ •$H_3$ $^+$N—S' --; and change "S—$CO_2^-$ .$H_3^{+N-S'}$ " to -- S—$CO_2^-$ •$H_3$ $^+$N—S'--;
Line 47, change "R—$CO_2^-$ $H_3$- $^+$N—S'" to -- R—$CO_2^-$ •$H_3$ $^+$N—S' --;
Line 48, change "S—$CO_2^-$ $H_3^+$N—S'" to -- S—$CO_2^-$ • $H_3$ $^+$N—S' --.

Column 3,
Line 3, change "GEM" to -- GAM --;
Line 8, change "R—$CO_2^-$ $H_3^+$N—S'" to -- R—$CO_2^-$ •$H_3$ $^+$N—S' --.
Line 13, change "S—$CO_2^-$ $H_3$ $^+$N—R'" to --S—$CO_2^-$ •$H_3$ $^+$N—R' --;
Line 35, change "GAMMBS" to -- GAM•MBA --;
Line 60, change "GAMMBA" to -- GAM•MBA --.

Column 4,
Line 8, change "GAMMBA" to --GAM•MBA --.
Line 10, change "GAMMBA" to --GAM•MBA --.
Line 12, change "GAMMBA" to --GAM•MBA --.
Line 16, change "R-GAMMBA" to -- R-GAM•MBA --;
Lines 36 and 37, change "S-GAMR-MBA" to -- S-GAM •R-MBA--;
Line 38, change "GAMMBA" to --GAM•MBA --;
Line 41, change "S-GAMMBA" to --GAM•MBA --;
Line 49, change "configuration $^{14.5}$ " to -- configuration $^{14,15}$ --.

Column 5,
Line 29, change "concentrate" to -- concentrated --.

UNITED STATES PATENT AND TRADEMARK OFFICE
CERTIFICATE OF CORRECTION

PATENT NO. : 6,051,734
DATED : April 18, 2000
INVENTOR(S) : Wildervanck et al.

It is certified that error appears in the above-identified patent and that said Letters Patent is hereby corrected as shown below:

Column 6,
Line 12, change "(R-BACHC1)" to (R-BAC·HC1) --;
Line 15, change "R-BACHC1" to -- R-BAC·HC1 --;
Line 16, change "BACHC1" to -- BAC·HC1 --;
Line 17, change "R-BACHC1" to -- R-BAC·HC1 --;
Line 21, (first line of Table) change "N salt R-GAMS-MBA" to
--N salt R-GAM·S-MBA--; and change "P salt S-GAMS-MBA" to
--P salt S-GAM·S-MBA--;
Line 36, change "concentrating" to -- concentration --.

Column 7,
Line 63, change "R-CO$_2$$^{-H}$$_3$+N-S'" to -- R—CO$_2^-$ ·H$_3^+$N—S' --.

Column 8,
Line 2, change "R-(+)-β-" to --R-(+)-α --;
Lines 17 and 18, change "S—CO$_2^-$ H$_3$+N-R'" to -- S—CO$_2^-$ ·H$_3^+$N—R' --.

Column 10,
Line 12, change "S' is" to -- R' is --.

Signed and Sealed this

Twenty-third Day of July, 2002

Attest:

JAMES E. ROGAN
Attesting Officer    Director of the United States Patent and Trademark Office